United States Patent [19]
Koch

[11] Patent Number: 5,824,074
[45] Date of Patent: Oct. 20, 1998

[54] INTRAOCCULAR LENS ARRANGEMENT AND METHOD FOR CORRECTING ASTIGMATISM

[76] Inventor: Hans-Reinhard Koch, Friedrich-Ebert Str. 23, Bonn, Germany, D-53177

[21] Appl. No.: 687,408
[22] PCT Filed: Feb. 2, 1995
[86] PCT No.: PCT/DE95/00135
  § 371 Date: Oct. 11, 1996
  § 102(e) Date: Oct. 11, 1996
[87] PCT Pub. No.: WO95/20926
  PCT Pub. Date: Aug. 10, 1995

[30] Foreign Application Priority Data

Feb. 3, 1994 [DE] Germany ............ 44 03 326.5

[51] Int. Cl.[6] .......................................... A61F 2/16
[52] U.S. Cl. ................................................. 623/6
[58] Field of Search ...................................... 623/6

[56] References Cited

U.S. PATENT DOCUMENTS

| | | | |
|---|---|---|---|
| 4,575,373 | 3/1986 | Johnson | 623/6 |
| 4,892,543 | 1/1990 | Turley | 623/6 |
| 4,932,971 | 6/1990 | Kelman | 623/6 |
| 4,963,148 | 10/1990 | Sulc et al. | 623/6 |
| 4,994,082 | 2/1991 | Richards et al. | 623/6 |
| 5,133,747 | 7/1992 | Feaster | 623/6 |
| 5,222,981 | 6/1993 | Werblin | 623/6 |
| 5,366,502 | 11/1994 | Patel | 623/6 |

FOREIGN PATENT DOCUMENTS

| | | | |
|---|---|---|---|
| 0 162 573 | 11/1985 | European Pat. Off. | 623/6 |
| 25 48 467 | 5/1977 | Germany . | |

*Primary Examiner*—Mary Beth Jones
*Attorney, Agent, or Firm*—Blank Rome Comisky & McCauley, LLP

[57] ABSTRACT

An intraocular lens structure for implantation in an eye of a patient has at least two intraocular lenses aligned along a common optical axis. Each of the intraocular lenses is provided with an optical compensation section adapted to correct an astigmatism with a linear orientation. A support retains each of the lenses for rotation about the common optical axis relative to one another when in an implanted state. The support may include a common haptic, or a separate haptic for respectively mounting each of the lenses together with a common ring for mounting each of the haptics to enable rotation of the lenses relative to one another after implantation. In the latter configuration, the common mounting ring has a pair of parallel grooves along an inner edge thereof for mounting the respective haptics therein for rotation of the lenses relative to one another. The lenses are provided with markings indicative of a preferred linear orientation thereof relative to one another about the axis when the lens structure is implanted. Each lens is composed of polymethymethacrylate (PMMA), silicone, hydrogel, or collapsible acrylate, and each optical compensation section has an optical cylindrical or torical effect.

17 Claims, 1 Drawing Sheet

INTRAOCCULAR LENS ARRANGEMENT AND METHOD FOR CORRECTING ASTIGMATISM

BACKGROUND OF THE INVENTION

If a blurred eye lens is removed within the scope of cataract surgery, it is generally replaced with an implanted intra-ocular lens today. After first calculating the optical constants of the eyes, the intra-ocular lens can be designed so that it corrects the existing refraction error, such as shortsightedness, farsightedness, and also astigmatism. At the respective wish of the patient, the intra-ocular lens can be chosen in such a way that a particular postoperative defect in vision exists, such as a weak shortsightedness that would enable the patient to see close up without additional correction.

While a spherical defect in vision, i.e., shortsightedness or farsightedness, can easily be corrected, the correction of an astigmatism still remains a problem today. In that connection it is important to know not only that an astigmatism can exist before the operation is undertaken to implant an intra-ocular lens, but that an astigmatism can also be produced as a side-effect of the operation, especially as the result of an operation incision and the incision sutures that later heal. In the recent past it is true that they have succeeded in reducing the problem of an operation-produced astigmatism through improved incision techniques; but the elimination of a potential astigmatism is not possible. As a result, it is a fact that each cataract operation is per se an astigmatism-producing operation, which, if the occasion should arise, can also be drawn upon to reduce the natural astigmatism caused by the geometry of the eye. In so far as an operating surgeon induces a typical postoperative astigmatism with a technique chosen by him, the residual total astigmatism could be corrected at least theoretically after the operation by inserting an intra-ocular lens with a compensation section to correct the astigmatism in such a way that the postoperative residual total astigmatism is corrected. It is, however, the case that the techniques of cataract surgery are so variable that an exact prediction of the residual total astigmatism after the operation is not yet possible. For this reason, it is not yet possible today to guarantee the elimination of postoperative astigmatism.

An intra-ocular lens arrangement with several intra-ocular lenses arranged one behind the other along a common axis is already known from U.S. Pat. No. 5,222,981. The lens arrangement consists of a basic lens, a covering lens, and a sandwich lens lying between the two. Especially this sandwich lens can be provided with a section through which an astigmatism can be corrected. The total lens arrangement is implanted in the eye, whereby the sandwich and the covering lens do not, at this stage, need to be provided with a section that is suitable for correcting a defect in vision. Only after the surgical operation to implant the lens has healed are the covering lens and the sandwich lens removed and replaced by the new lenses correcting the defect in vision. These lenses are certainly smaller than the total lens arrangement, but the second surgical operation is almost as serious as the one necessary for the implantation, for an incision several millimeters long must be carried out.

An intra-ocular lens arrangement made of a basic lens and a covering lens, which is also suitable for correcting an astigmatism, is known from U.S. Pat. No. 5,133,747. When the implantation is made, at first only the basic lens is implanted, and then subsequently the covering lens is put on, e.g., stuck on, in a smaller surgical operation. This covering lens then serves to correct the defect in vision, including an astigmatism. In this case as well, a second surgical operation is necessary, even when the operative astigmatism caused by the first surgical operation is relatively well compensated by this procedure. The procedure of sticking on the additional covering lens, however, requires high operative skills.

An intra-ocular lens for correcting an astigmatism is known from U.S. Pat. No. 4,512,039, which consists solely of a single torically cut intra-ocular lens. To reduce the postoperative astigmatism estimates of the astigmatism are made from empirical data, and the intra-ocular lens is inserted in such a way that the astigmatism is more or less compensated. This requires, however, that the operating surgeon knows the expected astigmatism quite well as a result of his operation methods.

SUMMARY OF THE INVENTION

The problem which the invention intends to solve is to specify an intra-ocular lens arrangement with which the postoperative residual astigmatism can be corrected with optimal results.

The present invention constitutes an improvement over the known intra-ocular lens arrangement in which a structure is made up of several intra-ocular lenses arranged one behind the other on a common optical axis, and at least one of the intra-ocular lenses is provided with an optical section to compensate for astigmatism.

In accordance with this, the basic idea of the invention consists of a lens arrangement with two intra-ocular lenses arranged one behind the other on the same optical axis, each of which displays a compensation section for correcting an astigmatism and whose section orientation is rotated against each other in the eye in such a way that the astigmatism is corrected. After the operation incision has healed, a final correction can be undertaken by inserting the two intra-ocular lenses into the eye through a small incision that does not change the astigmatism and then readjusting them by rotating them a little against one another.

A section with the optical effect of a cylindrical lens or a section with a toric effect is used as a compensation section.

This can, for instance, be a cylindrical section, which can be combined with a spherical section to compensate for another defect in vision, a toric section, or a section producing a diffraction (cf U.S. Pat. No. 5,100,226 in connection with the latter). Also possible are intra-ocular lenses made of a flexible material, whose form can be changed to obtain an optical cylindrical effect through the corresponding effect of the force; consider, for instance, the patent WO 92/03989, in which the form of the lens can be influenced by small actuators made of a ferromagnetic material and arranged in a mounting ring serving as a haptic for the intra-ocular lens.

The lens arrangement displays, for instance, two cylindrical lenses with a spherical-cylindrical cut arranged around the same optical axis so they can rotate; the spherical-cylindrical cut has a cylindrical effect, which depends only slightly on the implantation site of the lens in the eye and is fundamentally the same for both. The diopter values of both lenses for the cylindrical effect can display like or unlike signs. If these lenses are rotated against each other around the optical axis in such a way that their axes and strongest refracting meridians lie over one another every time the diopter values display unlike signs or if the lenses are rotated against each other by 90 degrees when the diopter values display like signs, then the cylindrical lenses compensate each other and only the spherical section has an effect. If the intra-ocular lenses are rotated against one another out of this position by 90 degrees so that, given unlike or like signs, the axis of one lens coincides with the strongest refracting meridians of the other lens or is rotated against the other lens by 90 degrees, then a maximal cylindrical effect with respect to the sum of the cylindrical effects of both individual lenses of the system arises in addition to the spherical effect. Variable astigmatism values can be adjusted between zero and the maximal value mentioned by adjusting both of the lenses to a position between these two extreme states.

Because the refractive power of a fracture-shaped incision of the lens, which is set up in front of a cylindrical lens, obeys a cosine-square relationship, two cylindrical lenses laid over each other thus have the effect of the sum of both cosine-square curves. Such a lens arrangement, designated as a cylindrical compensator, should therefore be able to take on all the values between a maximal cylinder value corresponding to the sum of the cylinder refractive powers of both lenses and the value of zero as the other extreme by rotating them respectively around the optical axis.

The lens arrangement is adjusted during the implantation to a correction value corresponding approximately to the expected postoperative astigmatism. Residual deviations after the operation can then be eliminated in a second minimal operation by rotating one or both intra-ocular lenses around the optical axis through a small incision. In clinical applications, such an intra-ocular lens arrangement could be realized as a cylindrical compensator in many ways. It is, preferably, made of two spherical-cylindrical lenses, whereby the lenses are mounted, for instance, in a common haptic and implanted with it, or each displays its own haptic and both lenses are implanted in the eye during the operation. With the current state of the operative techniques, the second variation is probably the preferred one so that, during such an operation, the lenses are put in the eye, whose haptic is mounted in the capsular sac, one after the other. The lens further back, turned toward the back of the eye, can, for example, have a more strongly bent haptic, while the front lens turned toward the cornea has a plane haptic or a weakly bent haptic. It is important that the haptic forms are chosen in such a way that the lenses in the eye remain capable of being both mobilized and rotated over a long period of time so that one can readjust an astigmatism that changes or arises later. The most suitable haptic in this connection seems to be a round haptic, whereby a further preferred working form is to implant a ring in the capsular sac equator, which serves as a guide track for the haptic of the intra-ocular lens or the lens arrangement to be implanted along which the haptics of the intra-ocular lenses can be adjusted. A similar mounting principle for a single intra-ocular lens is, for example, known from DE-A1-40 30 899.

The axis direction and the direction of the strongest refracting meridian are still, preferably, marked on each intra-ocular lens so that the operating surgeon immediately knows in which direction the lenses are to be rotated after the implantation. Such identification is also important so that, should the occasion arise, the operating surgeon can readjust the strength of the astigmatism at a later point in time.

A system made of two planoconvex lenses, whose plane sides face each other and whose compensation section is located in its convex side, is suggested as a preferred working form.

The spherical effect of the lens combination can generally be distributed alternately on both lenses or put on only one of the two lenses.

It is just as possible to design the lens combination with several strengths, for instance, for farsightedness or nearsightedness.

The lenses of the lens arrangement can be produced from any suitably hard or soft material, e.g., from polymethyl-methacrylate (PMMA), silicone, hydrogel, collapsible acrylate, etc.

BRIEF DESCRIPTION OF THE DRAWINGS

The above and other objects, features, aspects and attendant advantages of the invention will become apparent from a consideration of the following detailed description of the currently contemplated best mode of practicing the invention, with reference to presently preferred embodiments and methods thereof, taken in conjunction with the accompanying Figures of drawing, in which:

FIG. 5 represents a section through the ring used to mount the haptic according to FIG. 4 with a perspective trend sketched in.

DETAILED DESCRIPTION OF THE PREFERRED EMBODIMENTS AND METHODS

Figure 1:
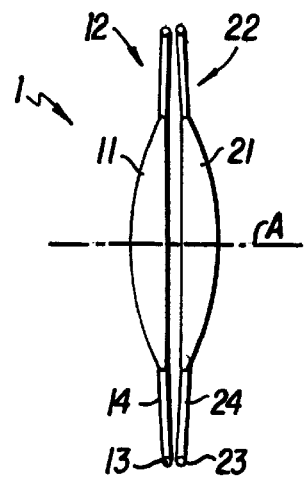
FIG. 1 represents a side view of a lens arrangement according to the invention, which is made of two intra-ocular lenses arranged one behind the other, each of which has a cylindrical section.

A lens arrangement shown in FIG. 1 consists of a front planoconvex intra-ocular lens (11) and a back intra-ocular lens (21) that is also planoconvex. The lenses have a common optical axis (A) and their plane sides are turned towards each other. Each intra-ocular lens (11 or 21) displays a haptic (12 or 22), which is designed here in each case as a ring haptic with an outer ring (13 and 23) and two crosspieces (14 and 24) each between lens and ring. The two haptics are arranged radially in such a way that they are mounted in the capsular sac of the eye.

Figure 3:
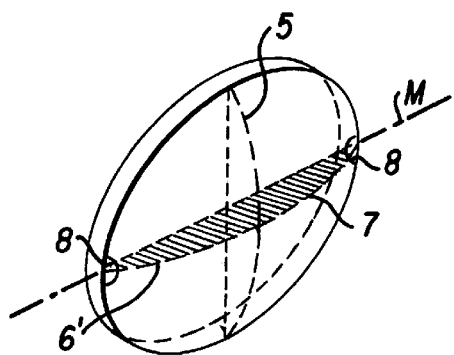
FIG. 3 is a diagrammatic, perspective view of the lens piece of an intra-ocular lens of the lens structure according to FIG. 1.

The lens piece of both intra-ocular lenses represented diagrammatically in FIG. 3 displays a sketched in spherical section (5) and, in addition, a cylindrical section (6) that is also sketched in, whose strongest refracting meridian is designated as (7) and whose meridian direction is designated as (M).

Figure 2:
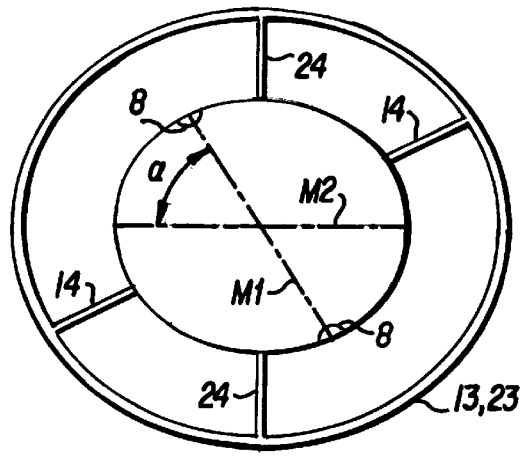
FIG. 2 represents a side view of a lens arrangement according to FIG. 1.

Both intra-ocular lenses (11 and 21) are, in accordance with FIG. 2, placed in the eye in such a way that the meridian direction (M1) of lens (11) together with the meridian direction (M2) of lens (21) form an angle designated in FIG. 2 as α. The particular median direction is indicated by two markings (8) lying across from one another, e.g., small holes, notches, or some other type of identification at the edge of the intra-ocular lenses.

Both intra-ocular lenses (11 and 21) can be rotated in their position to adjust the meridian direction by using a small tool, e.g., on the haptic or—if available—on the notches of holes mentioned.

The angle α between the meridian directions (M1 and M2) is then adjusted in such a way that the expected postoperative astigmatism is approximately compensated. After the operation incision heals, a readjustment can follow by means of a small manipulation tool, which is introduced into the eye through a micro-incision and with which the angle α between the meridian directions is adjusted in such a way that the astigmatism is completely corrected. Such a micro-incision has no influence on the astigmatism.

Figure 4:
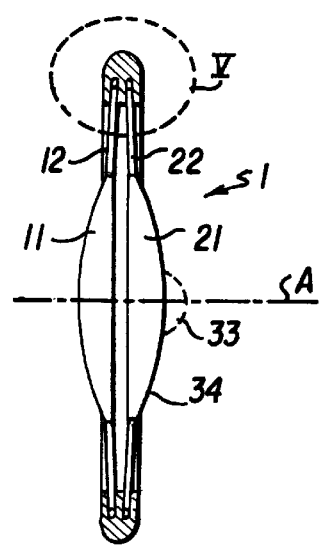
FIG. 4 represents a lens arrangement according to the invention, which is made of two intra-ocular lenses whose haptic is mounted in a common ring.
Figure 5:
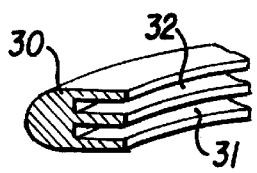

In FIG. 4 a modified working example of a lens structure (1') according to the invention is represented. The lens structure again displays a front and back intra-ocular lens (11 and 21) with a spherical-cylindrical section, whereby both haptics (12 and 22) are mounted in a ring (30), which is implanted in the capsular sac. The ring (30) has two parallel grooves (31 and 32) along its inner edges, whereby the haptic (12) of the front intra-ocular lens (11) and the haptic (22) of the back intra-ocular lens (21) are mounted in groove (31) and groove (32), respectively. The haptics of both intra-ocular lenses can be rotated in grooves (31 and 32) or in ring (30) to adjust the meridian directions.

In FIG. 4 an area (33) with an additional spherical section is indicated by a dotted line for the front lens. This area can serve to aid seeing close up, while the correspondingly cut surrounding "external" area (34) aids seeing distant objects.

It is obvious that the lens arrangements shown here serve merely as working examples. Consequently, lenses can have other forms, other types of sections, and other haptics, etc., so long as one guarantees that the lenses display a particular arrangement of the compensation sections with respect to the given meridian direction so that the astigmatism can be corrected and exactly fine-tuned by adjusting the angles between these meridian directions.

The lens arrangement can be produced with any suitable hard or soft material, e.g., PMMA, silicone, elastic hydrogel, collapsible acrylate, etc.

I claim:

1. An intraocular lens structure for implantation in an eye of a patient, the intraocular lens structure comprising a plurality of at least two intraocular lenses aligned along a common optical axis, each of said at least two intraocular lenses being provided with an optical compensation section adapted to correct an astigmatism with a linear orientation, and support means for retaining each of said at least two intraocular lenses for rotation about the common optical axis relative to one another when in an implanted state.

2. The intraocular lens structure of claim 1, wherein said support means comprises a separate haptic for respectively mounting each of said at least two intraocular lenses, and a common ring for mounting each of the haptics to enable rotation of said at least two intraocular lenses relative to one another after implantation.

3. The intraocular lens structure of claim 2, wherein the common mounting ring has a pair of parallel grooves along an inner edge of the mounting ring, for mounting the haptics of said at least two intraocular lenses in said pair of parallel grooves for rotation relative to one another.

4. The intraocular lens structure of claim 1, wherein said plurality of intraocular lenses have markings indicative of a preferred linear orientation of the lenses relative to one another about said axis when the lens structure is implanted.

5. The intraocular lens structure of claim 1, wherein said plurality of intraocular lenses have indicia about their respective edges representative of a preferred relative orientation of the lenses about said axis when the lens structure is implanted.

6. The intraocular lens structure of claim 1, wherein each said optical compensation section has an optical cylindrical or torical effect.

7. The intraocular lens structure of claim 1, wherein each of said plurality of intraocular lenses comprises a material selected from a group consisting of polymethymethacrylate (PMMA), silicone, hydrogel, and collapsible acrylate.

8. The intraocular lens structure of claim 1, wherein at least one of said plurality of intraocular lenses comprises a multistrength lens.

9. A method for correcting astigmatism in a patient comprising the steps of implanting a plurality of at least two intraocular lenses in an eye of the patient so that the lenses are aligned along a common optical axis, each of said at least two intraocular lenses being provided with an optical compensation section adapted to correct an astigmatism with a linear orientation, retaining each of said at least two intraocular lenses in alignment for rotation about the common optical axis relative to one another when in an implanted state, and adjusting the relative orientation of said at least two intraocular lenses by rotation of one of said lenses about the common optical axis during the implantation to a correction value corresponding approximately to an expected postoperative astigmatism.

10. The method of claim 9, further including the step of subsequently further adjusting the relative orientation of said at least two intraocular lenses by rotation of one thereof about the common optical axis after the implantation, to substantially eliminate residual deviations.

11. The method of claim 9, wherein said at least two intraocular lenses are retained in alignment along the common optical axis by mounting each in a separate haptic, and mounting each of the haptics within a common mounting ring to enable rotation of said at least two intraocular lenses relative to one another during and after said implantation.

12. The method of claim 11, wherein the mounting ring has a pair of parallel grooves along an inner edge of the mounting ring, for mounting the haptics of said at least two intraocular lenses in said pair of parallel grooves for rotation relative to one another.

13. The method of claim 9, wherein said plurality of intraocular lenses have markings indicative of a preferred linear orientation of the lenses relative to one another about said axis after said implantation.

14. The method of claim 9, wherein each said optical compensation section has an optical cylindrical or torical effect.

15. The method of claim 9, wherein each of said plurality of intraocular lenses comprises a material selected from a group consisting of polymethymethacrylate (PMMA), silicone, hydrogel, and collapsible acrylate.

16. An implantable intraocular lens structure having several intraocular lenses arranged one behind the other on a common optical axis, and provided with an optical compensation section to compensate for astigmatism, characterized in that the lens arrangement comprises two intraocular lenses, each of which displays a compensation section suitable for correcting an astigmatism, with a linear orientation, and a common support mounting both of said two intraocular lenses for rotation of at least one of the mounted lenses about the common optical axis relative to the other mounted lens when in an implanted state.

17. The implantable intraocular lens structure of claim 16, wherein said common support comprises a separate haptic for respectively mounting each of said two intraocular lenses, and a common ring for mounting each of the haptics to enable rotation of said at least two intraocular lenses relative to one another in the respective haptic within the common ring after implantation.

* * * * *